US009938212B2

United States Patent
Pokrovski et al.

(10) Patent No.: US 9,938,212 B2
(45) Date of Patent: *Apr. 10, 2018

(54) INTEGRATED PROCESS TO COPRODUCE TRANS-1-CHLORO-3,3,3-TRIFLUOROPROPENE, TRANS-1,3,3,3-TETRAFLUOROPROPENE, AND 1,1,1,3,3-PENTAFLUOROPROPANE

(75) Inventors: Konstantin A. Pokrovski, Orchard Park, NY (US); Daniel C. Merkel, Orchard Park, NY (US); Haiyou Wang, Amherst, NY (US); Hsueh Sung Tung, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/432,300

(22) Filed: Mar. 28, 2012

(65) Prior Publication Data

US 2013/0261353 A1 Oct. 3, 2013

(51) Int. Cl.
*C07C 17/25* (2006.01)
*C07C 17/20* (2006.01)
(Continued)

(52) U.S. Cl.
CPC ............ *C07C 17/25* (2013.01); *C07C 17/206* (2013.01); *C07C 17/208* (2013.01); *C07C 17/21* (2013.01);
(Continued)

(58) Field of Classification Search
CPC ......... C07C 21/18; C07C 21/04; C07C 17/25; C07C 17/206; C07C 19/08; C07C 17/087; C07C 17/04
See application file for complete search history.

(56) References Cited

U.S. PATENT DOCUMENTS 5,574,192 A  11/1996  VanDerPuy et al.
5,616,819 A *  4/1997  Boyce et al. ................. 570/167
(Continued)

FOREIGN PATENT DOCUMENTS

EP  729932 A1 *  9/1996
EP  0919527 A1  6/1999
(Continued)

OTHER PUBLICATIONS

PCT ISR & Written Opinion issued in PCT/US2013/031869 dated Jun. 12, 2013.
(Continued)

*Primary Examiner* — Medhanit W Bahta
(74) *Attorney, Agent, or Firm* — Bruce O. Bradford

(57) ABSTRACT

Disclosed is an integrated manufacturing process to coproduce (E) 1-chloro-3,3,3-trifluoropropene, (E) 1,3,3,3-tetrafluoropropene, and 1,1,1,3,3-pentafluoro-propane starting from a single starting feed material or a mixture of unsaturated hydrochlorocarbon feed materials comprising 1,1,1,3-tetrachloropropene and/or 1,1,3,3-tetrachloropropene. The process includes a combined liquid or vapor phase reaction/purification operation which directly produces (E) 1-chloro-3,3,3-trifluoro-propene (1233zd (E)) from these feed materials, which may also include 240fa. In the second liquid phase fluorination reactor 1233zd (E) is contacted with HF in the presence of catalyst to produce 1,1,1,3,3-pentafluoropropane (245fa) with high conversion and selectivity. A third reactor is used for dehydrofluorination of 245fa to produce (E) 1,3,3,3-tetrafluoropropene (1234ze (E)) by contacting in the liquid phase with a caustic solution or in the vapor phase using a dehydrofluorination catalyst. This operation may be followed by one or more purification processes to recover the 1234ze (E) product.

6 Claims, 2 Drawing Sheets

(51) Int. Cl.
*C07C 17/38* (2006.01)
*C07C 17/383* (2006.01)
*C07C 17/395* (2006.01)
*C07C 17/21* (2006.01)

(52) U.S. Cl.
CPC ............ *C07C 17/38* (2013.01); *C07C 17/383* (2013.01); *C07C 17/395* (2013.01); *Y02P 20/125* (2015.11); *Y02P 20/582* (2015.11)

(56) References Cited

U.S. PATENT DOCUMENTS

| | | | |
|---|---|---|---|
| 5,811,603 A * | 9/1998 | Elsheikh ...................... | 570/166 |
| 5,895,825 A | 4/1999 | Elsheikh et al. | |
| 6,166,274 A | 12/2000 | Chen et al. | |
| 6,362,383 B1 | 3/2002 | Wilmet et al. | |
| 6,472,573 B1 | 10/2002 | Yamamoto et al. | |
| 6,844,475 B1 * | 1/2005 | Tung et al. ................... | 570/168 |
| 7,230,146 B2 | 6/2007 | Merkel et al. | |
| 7,485,760 B2 | 2/2009 | Wang et al. | |
| 7,592,494 B2 * | 9/2009 | Tung ....................... | B01J 27/10 570/153 |
| 2005/0020862 A1 * | 1/2005 | Tung et al. ................... | 570/164 |
| 2007/0238908 A1 | 10/2007 | Merkel et al. | |
| 2008/0051611 A1 * | 2/2008 | Wang et al. ................. | 570/166 |
| 2008/0103342 A1 * | 5/2008 | Wang et al. ................. | 570/256 |
| 2010/0072415 A1 | 3/2010 | Rao et al. | |
| 2010/0168482 A1 | 7/2010 | Rao et al. | |
| 2011/0201853 A1 * | 8/2011 | Tung ..................... | C07C 17/206 570/168 |
| 2011/0218370 A1 | 9/2011 | Elsheikh et al. | |
| 2011/0245549 A1 * | 10/2011 | Merkel et al. ................ | 570/157 |
| 2012/0059200 A1 | 3/2012 | Pokrovski et al. | |
| 2012/0271070 A1 | 10/2012 | Wang et al. | |
| 2013/0261353 A1 | 10/2013 | Pokrovski et al. | |

FOREIGN PATENT DOCUMENTS

| | | |
|---|---|---|
| EP | 0931783 A1 | 7/1999 |
| EP | 0940382 A1 | 9/1999 |
| EP | 1110935 A1 | 6/2001 |
| EP | 1116706 A1 | 7/2001 |
| JP | H11-199529 A | 7/1999 |
| JP | H11-228462 A | 8/1999 |
| JP | H11-279088 A | 10/1999 |
| JP | 2000-095714 A | 4/2000 |
| JP | 2001-172209 A | 6/2001 |
| JP | 2001-526624 A | 12/2001 |
| WO | 9708117 A1 | 3/1997 |
| WO | 9724307 A1 | 7/1997 |

OTHER PUBLICATIONS

EPO Extended European Search Report for Appln. No. 13768998.0 dated Oct. 15, 2015.
Jul. 26, 2016 (JP) Office Action—Application No. 2015-503320.

* cited by examiner

INTEGRATED PROCESS TO COPRODUCE TRANS-1-CHLORO-3,3,3-TRIFLUOROPROPENE, TRANS-1,3,3,3-TETRAFLUOROPROPENE, AND 1,1,1,3,3-PENTAFLUOROPROPANE

BACKGROUND TO THE INVENTION

The use of chlorofluorocarbons or hydrochlorofluorocarbons as foam-blowing agents has been banned due to concerns that their release damages the ozone layer. More recently, foam-blowing (addition of a volatile material to a polymeric mixture to cause a bubbled matrix which imparts insulation or cushioning value) has been accomplished through use of HFC-245fa; however, concern has been raised about the Global Warming Potential of this material.

Trans-1,3,3,3-tetrafluoropropene (HFO-1234ze (E)) and trans-1-chloro-3,3,3-trifluoropropene (HCFO-1233zd (E)), two low GWP molecules, have been identified as a new generation of more environmentally friendly blowing agents. Both molecules have other potential applications, such as for example, as solvents, refrigerants, aerosols, and as building blocks for making other fluorinated compounds. It is foreseeable that there will be a transition period during which all three products, i.e., HFO-1234ze (E), HCFO-1233zd (E), and HFC-245fa, will be needed. It is, therefore, desired to develop an integrated process in which all three products can be manufactured for efficiencies and synergies.

Methods for separately producing these three products are known in the prior art. U.S. Pat. No. 6,844,475, which is hereby incorporated herein as a reference, teaches a process for producing HCFO-1233zd in a liquid phase reaction at a temperature of less than 150° C. in the presence of a Lewis acid catalyst or mixture of Lewis acid catalysts, and hydrogen chloride and HCFO-1233zd formed in the reaction are continuously removed and the HCFO-12333zd is isolated.

The preparation of HFC-245fa is realized in a one-step process as disclosed in U.S. Pat. No. 5,574,192, or in a two-step process, as disclosed in WO 97/24307 and in U.S. Pat. No. 6,362,383. In a two-step process, HCC-240fa first reacts with hydrogen fluoride to give HCFO-1233zd, which reacts in a second step with hydrogen fluoride to give HFC-245fa.

The preparation of HFO-1234ze (E), from HFC-245fa is taught in U.S. Pat. Nos. 7,230,146 and 7,485,760, the disclosures of which are hereby incorporated herein by reference.

Accordingly, the present invention provides an integrated process to co-produce these three compounds (HCFO-1233zd, HFC-245fa, and HFO-1234ze), starting from one feed material, namely a tetrachloropropene, or mixtures of such compounds, and the production amount of each of the products can be easily adjusted depending on market demand by simple adjustments of the process.

SUMMARY OF THE INVENTION

Developing an economical process for the continuous preparation of HCFO-1233zd (E) and/or HFO-1234ze (E) has been a goal of research in this field for some time. It has now been found that HCFO-1233zd (E), HFO-1234ze (E), and HFC-245fa may be continuously and economically co-produced via an integrated manufacturing process. The integrated manufacturing process starts with a single or mixture of unsaturated hydrochlorocarbon feed materials, namely 1,1,1,3-tetrachloropropene and/or 1,1,3,3-tetrachloropropene. One benefit of this process is that it avoids intimate contact of the compounds 1233zd (E) and 245fa, which would otherwise form an azeotropic composition that makes it impossible to separate the components using conventional separation techniques such as distillation.

In one embodiment of the present invention, the compounds (a) HCFO-1233zd (E), (b) HFO-1234ze (E), and (c) HFC-245fa; are co-produced in an integrated process using three reactor lines, starting with a single or mixture of unsaturated hydrochlorocarbon feed materials, namely 1,1,1,3-tetrachloropropene and/or 1,1,3,3-tetrachloropropene.

Thus, one embodiment of the present invention is an integrated manufacturing process to coproduce HCFO-1233zd (E), HFO-1234ze (E), and HFC-245fa, starting from a single unsaturated hydrochlorocarbon feed material or mixture of such materials. The process includes a combined liquid or vapor phase reaction/purification operation which directly produces HCFO-1233zd (E). In the second liquid phase fluorination reactor HCFO-1233zd (E) is reacted with HF in the presence of catalyst to produce HFC-245fa, with high conversion and selectivity. Optionally, a third reactor is used for dehydrofluorination to produce HFO-1234ze (E) by contacting in the liquid phase with a caustic solution or in the vapor phase using a dehydrofluorination catalyst. This operation may be followed by one or more purification processes to recover the HFO-1234ze (E) product.

This process has an economical advantage to produce HCFO-1233zd (E) over those previously known because the HCFO-1233zd (E) product is produced in a first reactor with a high selectivity, thus avoiding the need for separating HCFO-1233zd (E) and HFC-245fa products which form an azeotropic composition that makes it difficult to separate using conventional separation techniques such as distillation, thereby resulting in high product yield losses.

The disclosed process also has an advantage in that it allows for great flexibility in producing different amounts of each compound by adjusting the fractionation or distribution of the crude streams from the first and second fluorination reactors.

The disclosed integrated manufacturing process is different from prior art because it also includes the ability to recycle unreacted starting materials to maximize raw material utilization and product yields. It also discloses the ability to isolate by-products that may be sold for commercial value.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

Disclosed is a fully integrated co-manufacturing process for making HCFO-1233zd (E), HFC-245fa, and HFO-1234ze (E). Overall the co-production is a three step process. The chemistry involves:

Step 1:

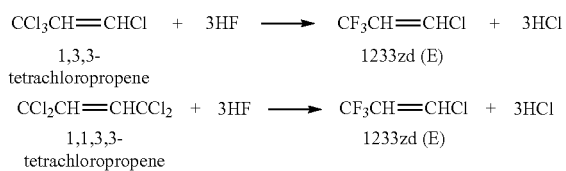

In Step 1, the reaction 1,1,3,3-tetrachloropropene and/or 1,3,3,3-tetrachloropropene, or mixtures thereof) with anhydrous HF in excess in a vapor phase or liquid phase reactor in such a way as to produce HCFO-1233zd (E) with a high selectivity (plus byproduct HCl). These reactions can be catalyzed or uncatalyzed.

Step 2:

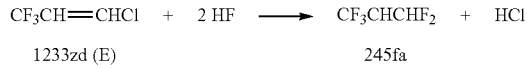

In Step 2, at least a portion of the produced HCFO-1233zd (E) can be recovered as a pure component (product) and another portion can be sent to a second fluorination reactor where it is fluorinated with HF in the liquid phase in the presence of a strong fluorination catalyst such as fluorinated SbCl$_5$ catalyst to produce a second product, HFC-245fa.

Step 3:

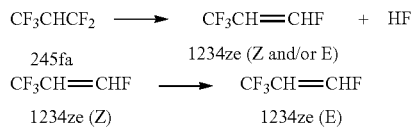

In Step 3, at least a portion of HFC-245fa produced in the second fluorination reactor can be recovered as a second desired pure component (product) and another portion can be dehydrofluorinated to produce the desired third pure component (product) HFO-1234ze (E). Also, as shown above, the Z-isomer (1234ze (Z)) can be converted to the desired trans-isomer 1234ze (E) through isomerization.

Figure 1:
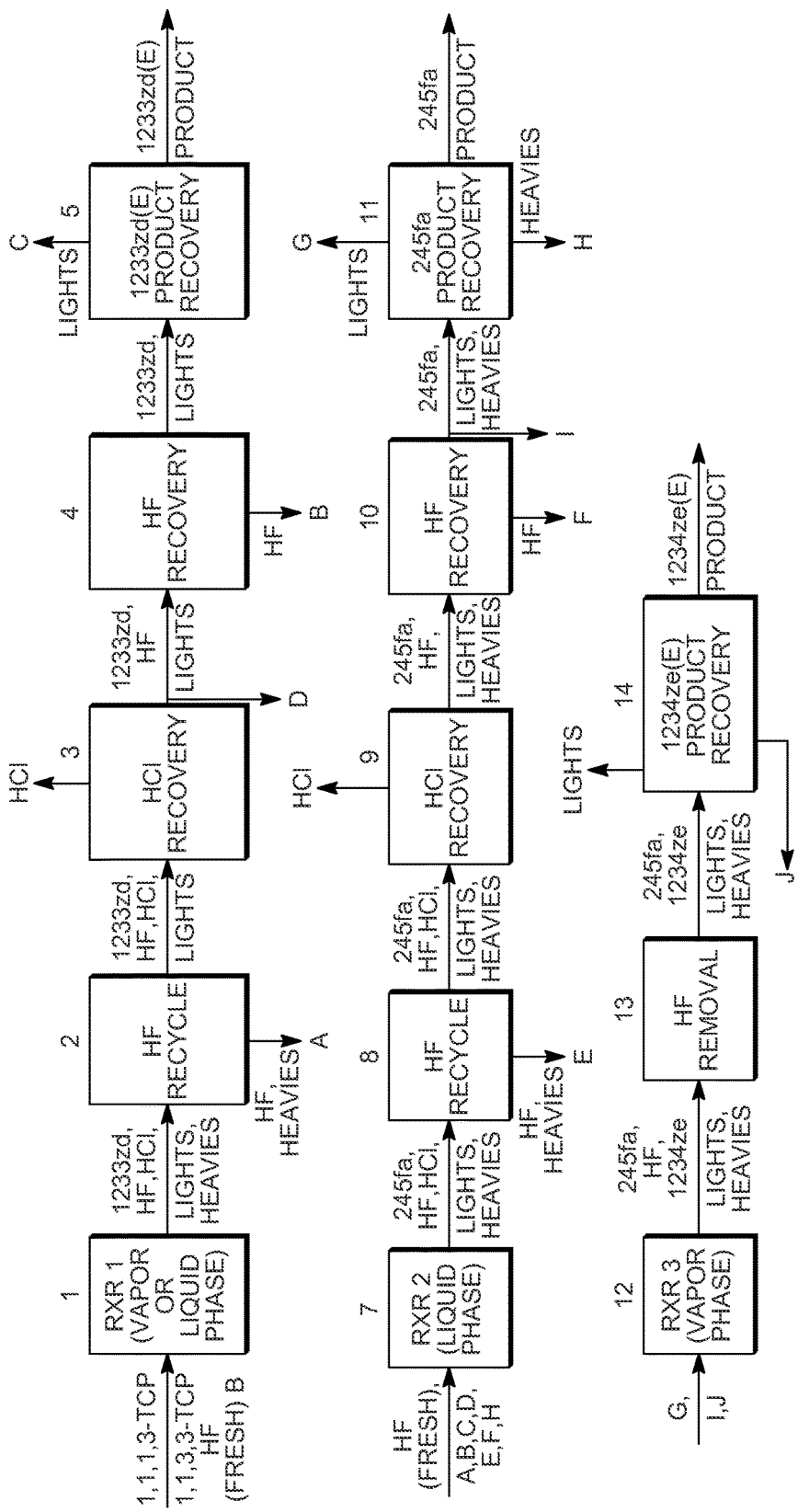
FIG. 1 shows the three integrated reactor lines used in one embodiment of the present invention.

The manufacturing process consists of the several major process operations as described below. The relative positions of these process operations in the three reaction lines are shown in FIG. 1.
(1) vapor or liquid phase fluorination reaction of 1,1,3,3-tetrachloropropene and/or 1,3,3,3-tetrachloropropene, and mixtures thereof using HF in a first reactor with simultaneous removal of byproduct HCl and the co-product 1233zd (E);
(2) separation of HF and heavy organics which are then fed to second fluorination reactor;
(3) separation and purification of byproduct HCl;
(4) separation of HF which is then fed to the second fluorination reactor,
(5) purification of first product, 1233zd (E);
(6) fluorination of 1233zd (E) with HF to produce the second co-product, 245fa, in a liquid phase catalyzed reactor;
(7) purification of the second co-product 245fa (with HCl recovery and HF recycle);
(8) dehydrofluorination of 245fa to 1234ze (E) in a third reactor (with recycle of unreacted 245fa and isomerization of 1234ze (Z) by-product); and
(9) purification of the third co-product, 1233zd (E).

These major process operations, as well as additional operations, are discussed in greater detail below.

The first fluorination reaction is conducted in a first reactor (RXR 1). This reaction can be conducted in the vapor phase in the presence of a vapor phase fluorination catalyst (such as fluorinated Cr$_2$O$_3$) or in the liquid phase. The liquid phase reaction can be run in the absence of the catalyst or in the presence of a liquid phase fluorination catalyst such as TiCl$_4$, FeCl$_3$.

If a vapor phase reactor is utilized, then the anhydrous HF and the feed(s) of 1,1,3,3-tetrachloropropene, or 1,3,3,3-tetrachloropropene, or mixtures thereof, are vaporized prior to entering the reactor. The product stream from the vapor phase reactor (1233zd (E), unreacted HF, and by-product HCl) are then fed to the recycle column (2). Preferably the reactor is constructed from materials which are resistant to the corrosive effects of the HF and catalyst, such as Hastelloy-C, Inconel, Monel, and Incoloy. Such vapor phase fluorination reactors are well known in the art.

For the liquid phase fluorination reaction, an agitated, temperature-controlled reactor is used for the contact of both feed materials and optionally with the liquid phase fluorination catalyst. The liquid phase fluorination reactor is preferably equipped with an integrated distillation column which permits the product to leave (along with byproduct HCl, traces of light organics [principally 1234ze (E+Z)], and HF in the amount of slightly above azeotropic composition), while retaining the bulk of the HF, plus under-fluorinated organics, plus, if used, the catalyst. Preferably the reactor is constructed from materials which are resistant to the corrosive effects of the HF and catalyst, such as Hastelloy-C, Inconel, Monel, Incoloy, or fluoropolymer-lined steel vessels. Such liquid-phase fluorination reactors are well known in the art.

The starting materials, 1,1,3,3-tetrachloropropene and/or 1,3,3,3-tetrachloropropene, or mixtures thereof and HF, are fed continuously into the first fluorination reactor. The reaction conditions (temperature, pressure, feed rates) and the HF to 1,1,3,3-tetrachloropropene and/or 1,3,3,3-tetrachloropropene ratio are adjusted to achieve the highest selectivity to 1233zd (E) product.

The stream exiting the first reactor (RXR 1) enters a recycle column. Here the high boiling under-fluorinated or over-fluorinated intermediates and some HF are separated and are fed to the second reactor (RXR 2) for further reaction. Crude 1233zd, HF, and HCl are fed forward in the integrated process.

The stream exiting the recycle column (2) is fed to an HCl recovery column. The HCl in this stream can then be purified and collected for sale using a low-temperature HCl distillation column. High purity HCl is isolated and can be absorbed in de-ionized water as concentrated HCl for sale.

The bottom stream from the HCl column (3) that contains a crude product mixture of 1233zd/lights and about 30 wt % to 50 wt % HF is fed to a sulfuric extractor or a phase separator for removal of HF from this mixture. HF is either dissolved in the sulfuric acid or phase separated from the organic mixture. HF is desorbed from the sulfuric acid/HF mixture by stripping distillation and recycled back to the reactor. The organic mixture either from the overhead of the sulfuric acid extractor may require treatment (scrubbing or adsorption) to remove traces of HF before it is fed to the 1233zd (E) product recovery train (5). Recovered HF is recycled back to first fluorination reactor (RXR 1) or is fed forward to second fluorination reactor (RXR 2).

The purification of first desired product 1233zd (E) is performed via distillation utilizing one or more of conventional distillation columns operating in a continuous mode. The purified first desired product, 1233zd (E) is collected and is available for sale. The lights and heavies are fed forward to the second fluorination reactor (RXR 2).

The reaction in RXR 2 uses a liquid phase fluorination catalyst of proper strength to achieve the desired reaction preferentially. It has been found that a catalyst comprised of antimony pentachloride (liquid under ambient conditions) which has been partially or totally fluorinated by the action of anhydrous HF achieves the desired degree of conversion without forming undesired byproducts. The catalyst fluorination is conducted by adding a specified amount of antimony pentachloride to a non-agitated, temperature-controlled reactor vessel, and adding HF by a gradual flow. A moderate amount of HCl will be generated in the operation. Conditions: 10° C. to 50° C. and at about 0 psig to 100 psig pressure. Additional fluorination catalysts that can be used include in combination with antimony pentachloride (all are partially of totally fluorinated by the action of anhydrous HF) $TiCl_4$, $TaCl_5$, $SbCl_3$.

Reaction Line 2 makes use of a reaction and stripping column. The key to this reaction is the equipment arrangement. A non-agitated, temperature-controlled reactor for the contact of both feed materials with the liquid catalyst and an integrated distillation column (operating in stripping mode) which permits the desired 245fa product to leave (along with byproduct HCl and sufficient AHF to form the azeotrope), while retaining the bulk of the HF, plus under-fluorinated and plus the catalyst is key.

Preferably the RXR 2 reactor is constructed from materials which are resistant to the corrosive effects of the HF and catalyst, such as fluoropolymer-lined steel vessels. Such liquid-phase fluorination reactors are well known in the art. Once the catalyst has been prepared, the reaction can be initiated immediately upon heating to the desired reaction temperature. The flow of HF for the catalyst preparation need not to be discontinued while the reactor is heated to a temperature of 85° C. to 115° C.

Preferably the HF feed is vaporized and superheated to provide the heat necessary to maintain proper reactor operating temperatures. Then the addition of the organic feed (1233zd) can be started immediately to cause continuous reaction while maintaining the flow of HF at an amount sufficient to produce the desired product plus an excess amount to account for losses due to azeotrope compositions of 245fa/HF that exit the top of the integrated distillation column. The reaction runs under HF rich conditions to produce the reaction product, 245fa.

Proper temperature control of the coolant and sufficient reflux action are necessary for the stripping column to be effective. General operating conditions which have been found to work well for the reaction and stripping are:

(a) operating pressure of 80 psig to 140 psig maintained by a control valve on the exiting flow from the stripper column;
(b) reactor temperature of 85° C. to 115° C., primarily supplied by superheating the HF vapor feed with high-pressure steam to 120° C. to 150° C. directly into the reaction mixture and steam flow into the reactor jacket;
(c) application of brine cooling to the heat exchanger on top of the stripper column to induce reflux; temperature in the center portion of the stripper about 10° C. to 40° C. below that in the reactor;
(d) additional heat input; and
(e) feed rate of HF to maintain reactor and stripper conditions.

The stream exiting second reactor (RXR 2) enters a recycle column. Here the high boiling under-fluorinated or over-fluorinated intermediates and some HF are separated and are fed back to the second reactor (RXR 2) for further reaction. Crude 245fa, HF, and HCl are fed forward in the integrated process.

The stream exiting the recycle column (8) is fed to a HCl recovery column. The HCl in this stream can then be purified and collected for sale using a low-temperature HCl distillation column. High purity HCl is isolated and can be absorbed in de-ionized water as concentrated HCl for sale. Optionally water or caustic absorber can be used to remove HCl (and HF if this option is used) from the crude stream followed by a drying column.

The bottom stream from the HCl column (9) that contains a crude product mixture of 245fa/light ends and about 30 wt % to 50 wt % HF is fed to a sulfuric acid extractor for removal of HF from this mixture. HF is dissolved in the sulfuric acid and separated from the organic mixture. HF is desorbed from the sulfuric acid/HF mixture by stripping distillation and recycled back to the reactor. The organic mixture either from the overhead of the sulfuric acid extractor may require treatment (scrubbing or adsorption) to remove traces of HF before it is fed to the 245fa product recovery train (11) or fed forward to the third dehydrofluorination reactor (RXR 3). Recovered HF is recycled back to second fluorination reactor (RXR 2). This HF recovery step is not necessary if an absorber (water or caustic) was used above.

Purification of the second product, 245fa, consists of two continuously operating distillation columns. The first column is used to remove light ends, mainly 1234ze (E) from the 245fa and the second column is used to remove the heavier components. The light and heavy ends that are removed from the top of the first column and bottom of the second column can both be recycled back to an earlier processing step like step (7). Optionally light ends from the 245fa product recovery train, mainly 1234ze, can be fed to the dehydrofluorination reactor (RXR 3).

A portion of the stream from step (10), and the light ends from the first distillation column of step (11) are fed to one or more catalyzed vapor phase reactors where the 245fa is dehydrofluorinated to produce the desired 1234ze (E) product and HF. The reactor(s) contains dehydrofluorination catalyst such as fluorinated $Cr_2O_3$ that facilitates the conversion of 245fa into 1234ze (E). The reaction conditions (temperature, pressure, feed rates) are adjusted to achieve the highest yield to 1234ze (E) product. Preferably the reactor is constructed from materials which are resistant to the corrosive effects of the HF, such as Hastelloy-C, Inconel, Monel, Incoloy. The reactor effluent is fed forward to the HF recovery system (13). Optionally, the dehydrofluorination reaction is conducted in a liquid phase using caustic as a dehydrofluorinating agent. If this option is utilized, the product stream is fed to the 1234ze (E) product recovery system (14).

The product stream exiting the dehydrofluorination reactor (RXR 3) containing mainly 1234ze (E), 1234ze (Z), and 245fa is fed to the HF removal system. The HF from the crude 1234ze (E) stream is removed using a water or caustic absorption unit followed by a drying column (13). Optionally, sulfuric acid extraction system can be used to recover HF. The acid feed crude product stream is fed forward to 1234ze (E) product recovery train (14). The step of acid recovery is not needed if caustic solution was used in dehydrofluorination step (12).

Purification of third product 1234ze (E) consists of two continuously operating distillation columns. The first column is used to remove light ends (i.e., lights) that are sent to utilization. The second column is used to remove the heavier components (i.e., heavies). These heavy ends that are removed from the bottom of the second column, mainly 1234ze (Z) and unreacted 245fa, are recycled back to the dehydrofluorination reactor (RXR 3).

The following examples are provided to further illustrate the invention and should not be taken as limitations of the invention.

Example 1

For the experiment 450 grams of HF and 270 grams of the mixture of 50% 1,1,3,3-tetrachloropropene/50% 1,3,3,3-tetrachloropropene (15 to 1 mole ratio HF:organics) are charged to the reactor at room temperature. The mixer is then turned on ensuring the reactor contents are well mixed. Then the reactor is heated to 140° C., this temperature is maintained until the completion of the reaction that is indicated by the lack of HCl generation. The reactor pressure is controlled in the range of 450 psig to 480 psig by venting off the HCl generated in the reaction to a dry-ice chilled dry ice trap (DIT). At the completion of the reaction after about 4.5 hours, as determined by a lack of HCl generation, the pressure from the reactor is vented into the DIT.

The crude product from the DIT is transferred into a 2 L Monel absorption cylinder (frozen in dry-ice) with about 700 grams of water. The absorption cylinder is allowed to warm up to room temperature and a sample of an organic layer that is formed in the cylinder (aqueous and organic layers are present in the cylinder upon discharge) is taken and analyzed by GC. GC results indicate the following composition of the reaction products 2.48 GC % 245fa, 92.61 GC % 1233zd (E), 0.22 GC % 244fa, 2.93 GC % 1233zd (Z). The amount of organic collected is later quantified by further analysis of the different phases and amounted to 170 grams.

The organic remaining in the reactor after venting is recovered by quenching the reactor with about 300 to 400 grams of water to absorb HF and HCl, and then adding about 100 grams of carbon tetrachloride. The reactor contents are discharged into a plastic bottle. The organic is separated from the aqueous phase by use of a reparatory funnel. The amount of heavies collected from the reactor is calculated by subtracting the weight of CCl4 added to the reactor from the total weight of organic phase collected and amounts to 14.9 grams. GC/MS and GC analysis of the organic layer follows and reveals 3 distinct peaks attributed to under-fluorinated species HCFC-241fa, 94.057 GC %, HCFC-242fa, 1.760 GC %, and the starting materials (tetrachloropropenes), 4.183 GC %.

Example 2

Dehydrofluorination of 245fa

The reaction was conducted in a two inch inner diameter Monel packed-bed reactor charged with 760 mL of fluorinated $Cr_2O_3$ catalyst. The crude product stream exiting the reactor was fed to KOH scrubber and then to a single distillation column operating in a continuous mode. The 1234ze (E) product together with light impurities was collected as a distillate from the top of the distillation column. The stream consisting mainly of unreacted 245fa and 1234ze (Z) by-product was recycled back to the reactor from the bottom of the reboiler. The reaction was conducted at catalyst bed temperature of 240° C. to 290° C. (coldest at the reactor inlet), at a reactor pressure of 5.2 psig, a constant 245fa feed rate of 1.2 lb/h, a recycle feed rate varied between 0.8 to 0.98 lb/h to maintain a constant liquid level in reboiler, and a constant overhead take-off rate of 1.02 lb/h (which is equivalent to a trans-1234ze productivity of 38 $lb/ft^3/hr$).

Figure 2:
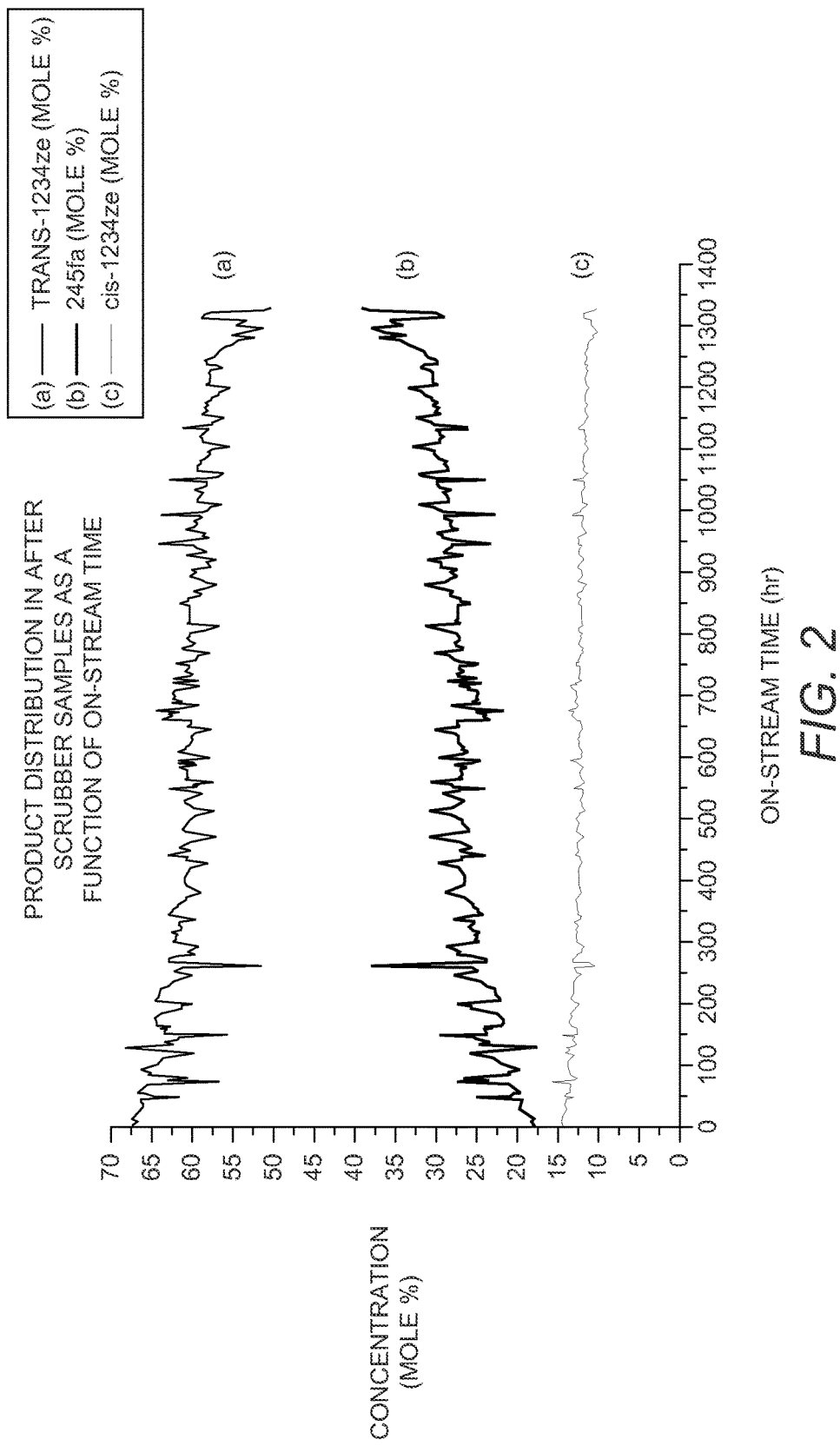
FIG. 2 illustrates the product distribution in "after scrubber" samples as a function of on-stream time. The top line is trans-HFO-1234ze (mole %); the middle line is HFC-245fa (mole %) and the bottom line is cis-HFO-1234ze (mole %).

During continuous operation, feeds and products at different sampling ports were periodically analyzed. Table I below presents the results obtained at different reaction stages. The overhead product contains 40 ppm to 100 ppm 1234yf, 400-500 ppm trifluoropropyne, 99.9+% trans-1234ze, and about 70 ppm 1234zc, indicating one distillation column is not efficient enough for product separation. See also, FIG. 2.

TABLE I

Compositions of recycle feed, combined feed, and products at different sampling ports

| | | Feeds | | Products | | |
|---|---|---|---|---|---|---|
| Component | Time on stream H | Recycle stream Mol % | Combined stream mol % | Before scrubber mol % | After scrubber mol % | Overhead mol % |
| 1234yf | 180-200 | 0.0000 | 0.0000 | 0.0079 | 0.0073 | 0.0104 |
| 3,3,3-trifluoropropyne | | 0.0000 | 0.0000 | 0.0274 | 0.0504 | 0.0068 |
| trans-1234ze | | 0.0875 | 0.0198 | 59.9176 | 64.0869 | 99.9148 |
| 1234zc | | 0.0448 | 0.0089 | 0.0387 | 0.0312 | 0.0067 |
| 245fa | | 62.9943 | 89.7248 | 27.8974 | 22.6660 | 0.0000 |
| cis-1234ze | | 36.7607 | 10.2093 | 12.0646 | 13.1091 | 0.0000 |
| Others | | 0.1127 | 0.0372 | 0.0465 | 0.0490 | 0.0000 |
| 1234yf | 630-650 | 0.0000 | 0.0000 | 0.0026 | 0.0035 | 0.0050 |
| 3,3,3-trifluoropropyne | | 0.0000 | 0.0000 | 0.0173 | 0.0341 | 0.0468 |
| trans-1234ze | | 0.0602 | 0.0780 | 56.4184 | 60.0081 | 99.9482 |
| 1234zc | | 0.0372 | 0.0111 | 0.0341 | 0.0306 | 0.0000 |
| 245fa | | 69.0474 | 88.6978 | 32.1915 | 27.4337 | 0.0000 |
| cis-1234ze | | 30.6267 | 11.1300 | 11.2364 | 12.3887 | 0.0000 |

TABLE I-continued

Compositions of recycle feed, combined feed, and products at different sampling ports

| Component | Time on stream H | Feeds Recycle stream Mol % | Combined stream mol % | Products Before scrubber mol % | After scrubber mol % | Overhead mol % |
|---|---|---|---|---|---|---|
| Others |  | 0.2285 | 0.0831 | 0.0996 | 0.1015 | 0.0000 |
| 1234yf | 1240-1280 | 0.0000 | 0.0000 |  | 0.0016 | 0.0039 |
| 3,3,3-trifluoropropyne |  | 0.0000 | 0.0475 |  | 0.0255 | 0.0429 |
| trans-1234ze |  | 0.0958 | 0.0000 |  | 56.5567 | 99.9531 |
| 1234zc |  | 0.0393 | 0.0184 |  | 0.0278 | 0.0067 |
| 245fa |  | 72.3724 | 85.9086 |  | 31.8216 | 0.0000 |
| cis-1234ze |  | 27.3347 | 13.9411 |  | 11.4973 | 0.0000 |
| Others |  | 0.1578 | 0.0844 |  | 0.0695 | 0.0001 |

Example 3

This example illustrates continuous distillation of the crude mixture consisting essentially of HFO-1234ze (E), HFO-1234ze (Z), and HFC-245fa that was produced in Example 2.

The distillation column consisted of a ten gallon reboiler, two inch inner diameter by ten foot column packed with propack distillation packing and a shell and tube condenser. The column had about 30 theoretical plates. The distillation column was equipped with reboiler level indicator; temperature, pressure, and differential pressure transmitters. The distillation was run at pressure of about 50 psig and differential pressure of about 17 inches of $H_2O$ in the continuous mode.

The feed consisting essentially of HFO-1234ze (E), HFO-1234ze (Z), HFC-245fa, and small amount of impurities was continuously fed via the inlet port at the bottom of the distillation column at the rate of about 1.75 lb/hr. The distillate consisting essentially of HFO-1234ze (E) and light impurity was collected from the top of the condenser at the rate of about 1.02 lb/hr. The stream consisting essentially of HFC-245fa and HFO-1234ze (Z) (see Table II below) was continuously taken out from the bottom of reboiler at the rate of about 0.73 lb/hr in order to maintain the level of material in the reboiler at about 40%. The distillation was run continuously for about 1000 hours.

TABLE II

Composition of 1234ze (E) distillation column streams

|  | 3,3,3-trifluoropropyne Wt. % | HFO-1234ze (E) Wt. % | HFO-1234zc Wt. % | HFO-1234ze (Z) Wt. % | HCFO-1233zd Wt. % | HFC-245fa Wt. % |
|---|---|---|---|---|---|---|
| Feed composition | 0.0263 | 58.1003 | 0.0253 | 11.3939 | trace | 30.4542 |
| Distillate composition | 0.0497 | 99.9503 | 0.0000 | — | — | — |
| Bottoms composition | — | 0.0801 | 0.0604 | 27.1886 | trace | 72.6709 |

Example 4

This example illustrates the semi-batch reaction where HF is continuously fed into a charge of titanium tetrachloride catalyst and a mixture of 50% 1,1,3,3-tetrachloropropene/50% 1,3,3,3-tetrachloropropene.

A clean, empty ten gallon jacketed, agitated reactor of Hastelloy C construction is prepared. This reactor is connected to a two inch inner diameter vertical, PTFE-lined pipe containing packing material (stripper), which is in turn connected to an overhead heat exchanger. The heat exchanger is supplied with −40° C. brine circulation on the shell side. Vapors exiting this stripper are processed through a scrubber, in which temperature-controlled dilute potassium hydroxide aqueous solution is circulated. Vapors exiting this stripper are collected in a weighed, chilled (−40° C.) cylinder referred to as the product collection cylinder (PCC), followed by a smaller cylinder in series chilled in a dry ice bath.

For this example, 14 lbs. of anhydrous HF are first charged to the reactor for the purpose of assuring complete fluorination of the fluorination catalyst. Next, 1.5 lbs. of $TiCl_4$ fluorination catalyst are added to the reactor. HCl is immediately generated as catalyst fluorination ensues as observed by the build-up of pressure in the reactor. After the pressure is reduced by venting most of the HCl from the system, 50 lbs of a 50% 1,1,3,3-tetrachloropropene/50% 1,3,3,3-tetrachloropropene mixture is added batch wise. The reactor is then heated. At about 85° C. HCl starts to be generated indicating that the fluorination reaction is initiated. The system pressure is controlled at about 120 psig. Additional HF is then fed continuously and product is collected in the PCC until the 50% 1,1,3,3-tetrachloropropene/50% 1,3,3,3-tetrachloropropene mixture is consumed.

The GC analysis of the crude material that was collected in the PCC during the run is as follows; 86.4% 1233zd (E); 5.5% G-244fa; 3.1% 1234ze (E); 1.5% 1233zd (Z); 1.1% 1234ze (Z); 1.1% dimer; 0.2% trifluoropropyne.

Example 5

This example illustrates the recovery of anhydrous HF from a mixture of HF, HCFO-1233zd, and 50% 1,1,3,3-tetrachloropropene/50% 1,3,3,3-tetrachloropropene mixture according to certain preferred embodiments of the present invention.

A mixture consisting of about 70 wt. % HCFO-1233zd (E) and about 30 wt. % HF is vaporized and fed to the bottom of a packed column at a feed rate of about 2.9 lbs per hour for about 4 hours. A stream of about 80 wt. % sulfuric acid (80/20 $H_2SO_4/H_2O$) with about 2% HF dissolved therein is fed continuously to the top of the same packed column at a feed rate of about 5.6 lbs per hour during the same time frame. A gaseous stream exiting the top of the column comprises HCFO-1233zd (E) with less than 1.0 wt. % HF therein. The concentration of HF in the sulfuric acid in the column bottoms increases from 2.0 wt. % to about 15 wt. %.

The column bottoms containing sulfuric acid and about 15 wt. % HF is collected and charged into a two gallon Teflon® lined vessel. The mixture is heated to about 140° C. to vaporize and flash off HF product, which is collected. The collected HF product contains about 6000 ppm water and 500 ppm sulfur. The sulfuric acid contains about 500 ppm of TOC (total organic carbon).

The HF collected from flash distillation is distilled in a distillation column and anhydrous HF is recovered. The recovered anhydrous HF contains less than 50 ppm of sulfur impurities and lees than 100 ppm water

Example 6

This example demonstrates the purification of the acid free 1233zd (E) crude product. 92 lbs of acid free 1233zd crude material produced in Example 2 is charged to a batch distillation column. The crude material contains about 94 GC area % and 6 GC area % impurities. The distillation column consists of a 10 gallon reboiler, two inch inner diameter by 10 feet propack column, and a shell and tube condenser. The column has about 30 theoretical plates. The distillation column is equipped with temperature, pressure, and differential pressure transmitters. About 7 lbs of a lights cut is recovered which consists of mainly 1234ze (Z+E), trifluoropropyne, 245fa, and 1233zd (E). 82 lbs of 99.8+ GC area % 1233zd (E) are collected. The reboiler residue amounting to about 3 lbs is mainly 244fa, 1233zd (Z), 1233zd dimmer, and 1233zd (E). The recovery of 99.8+ GC area % pure 1233zd (E) is 94.8%.

Example 7

In this example, a continuous liquid phase fluorination of a mixed stream containing 1233zd (Z) and 1233zd (E) is demonstrated. The fluorination catalyst for the example is $SbCl_5$.

6500 grams of $SbCl_5$ are contained in a Teflon®-lined liquid phase reactor equipped with a catalyst stripper, two inch inside diameter packed column and with a condenser whose function is to return entrained catalyst, some of the unreacted HF and some of the unreacted organic back to the reactor when the system is running in continuous reaction mode. The reactor is 2.75-inch inside diameter×36-inch long and is not equipped with a mixer/agitator. The reactor is heated to about 85° C. to 87° C. The catalyst is then activated by the addition of 1500 grams of HF followed by 1500 grams of $Cl_2$. HCl generated by the fluorination of the catalyst raises the reaction system pressure to about 100 psig where it is controlled.

The continuous gaseous HF feed is started first. It is bubbled into the liquid catalyst through a dip tube at a rate of 1.9 lb/hr, and when 1.0 lb of HF has been added, the mixed organic feed stream is introduced. It also enters the liquid catalyst by way of a dip tube and consist of about 95% 1233zd (E) and 5% 1233zd (Z). The mixed organic is fed continuously at rate of 2.0 lb/hr. The mole ratio of HF to organic raw material is 7:1. The reaction temperature is maintained at 90° C. to 95° C. and the pressure is maintained at 120 psig. 245fa, unreacted organic, organic by-products, HCl, and unreacted HF exit the top of the catstripper column. The experiment is run continuously for over 500 hours and the average conversion of the organic raw material is greater than 99.5% while the selectivity to 245fa reaches 99.5%. $Cl_2$ (0.02 mole/mole organic) is continuously fed into the reaction mixture on a periodic basis through a dip tube in order to keep the catalyst active.

Example 8

245fa crude material exiting a 50 gallon pilot plant fluorination reaction system was contacted with water in an absorption column to remove HCl and HF. Only a trace amount of acid remained. This stream was then contacted by a dilute caustic stream in a second absorber removing the remaining acid. The stream was then passed through a column containing X13 molecular sieves to remove any moisture that was added to the stream during contact with water during the acid removal step.

Example 9

The dried and acid free 245fa crude material from Example 8 was then distilled continuously to greater than 99.95% purity using a series of two conventional distillation columns to remove most of the low and high boiling impurities.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for making trans-1-chloro-3,3,3-trifluoropropene (HCFO-1233zd (E)), 1,1,1,3,3-pentafluoropropane (HFC-245fa), and trans-1,3,3,3-tetrafluoropropene (HFO-1234ze (E)) in three continuously operated steps comprising:

(a) conducting a fluorination reaction of 1,1,3,3-tetrachloropropene and 1,3,3,3-tetrachloropropene in a fluorination reactor with excess anhydrous HF to produce a first product HCFO-1233zd (E) with high selectivity;
(b) fluorinating the produced HCFO-1233zd (E) with HF in a liquid phase in the presence of a fluorination catalyst to produce a second product HFC-245fa;
(c) dehydrofluorinating the produced HFC-245fa in a vapor phase using fluorinated $Cr_2O_3$ catalyst to produce a third product comprising HFO-1234ze (E); and
(d) scrubbing the third product comprising HFO-1234ze (E);
and wherein during the continuously operated process in Step (d) products are generated as follows:
(1) during time on stream of from 180 to 200 hours, about 64.1 mole percent of trans-1234ze, about 22.7 mole percent of 245fa, and about 13.1 mole percent of cis-1234ze;
(2) during time on stream of from 630 to 650 hours, about 60.0 mole percent of trans-1234ze, about 27.4 mole percent of 245fa, and about 12.4 mole percent of cis-1234ze; and
(3) during time on stream of from 1240 to 1280 hours, about 56.6 mole percent of trans-1234ze, about 31.8 mole percent of 245fa, and 11.5 mole percent of cis-1234ze.

2. The process of claim 1, wherein the cis-isomer, 1234ze (Z), formed in in Step (d), is converted to the desired trans-isomer 1234ze (E) by an isomerization reaction.

3. The process of claim 1, wherein the Step (a) fluorination reaction is conducted in a liquid phase and wherein the fluorination reactor further includes an integrated distillation column for removal of the 1233zd (E) product.

4. The process of claim 1, wherein Step (a) further comprises a purification step of the produced 1233zd (E) by distillation.

5. The process of claim 1, wherein step (b) is conducted in a second reactor using antimony pentachloride as the fluorination catalyst, which has been partially or totally fluorinated, and wherein the second reactor further includes using a distillation column for isolation of the 245fa product.

6. The process of claim 1, wherein the third product 1234ze (E) of Step (d) is further purified by distillation.

* * * * *